United States Patent
Ricci et al.

(10) Patent No.: US 6,419,491 B1
(45) Date of Patent: Jul. 16, 2002

(54) DENTAL IMPLANT SYSTEM WITH REPEATING MICROGEOMETRIC SURFACE PATTERNS

(75) Inventors: John Ricci, Middleton; Harold Alexander, Short Hills, both of NJ (US); Charles Naiman, deceased, late of Brookline, MA (US), by Harriet Naiman, executrix; Bruce L. Hollander, Boca Raton; Ingo K. Kozak, Atlantis, both of FL (US)

(73) Assignee: Bio-Lok International, Inc., Deerfield Beach, FL (US)

( * ) Notice: Subject to any disclaimer, the term of this patent is extended or adjusted under 35 U.S.C. 154(b) by 0 days.

(21) Appl. No.: 09/500,038

(22) Filed: Feb. 8, 2000

Related U.S. Application Data

(63) Continuation-in-part of application No. 08/996,244, filed on Dec. 22, 1997, now abandoned, which is a continuation-in-part of application No. 08/639,712, filed on Apr. 29, 1996, now abandoned, which is a continuation of application No. 08/390,805, filed on Feb. 15, 1995, now abandoned, which is a continuation of application No. 08/146,790, filed on Nov. 2, 1993, now abandoned.

(51) Int. Cl.[7] .................................................. A61C 8/00
(52) U.S. Cl. ...................................................... 433/173
(58) Field of Search ................................ 433/173, 174, 433/175, 201.1; 623/17.17, 17.18, 23.5, 23.76

(56) References Cited

U.S. PATENT DOCUMENTS

| | | |
|---|---|---|
| 4,553,272 A | 11/1985 | Mears |
| 4,826,434 A * | 5/1989 | Krueger |
| 5,202,227 A | 4/1993 | Matsuda |
| 5,588,838 A * | 12/1996 | Hansson et al. ............. 433/173 |
| 5,607,607 A | 3/1997 | Naiman |
| 5,716,412 A * | 2/1998 | DeCarlo, Jr. et al. ...... 623/23.5 |
| 5,833,641 A | 11/1998 | Curtis |
| 5,976,826 A | 11/1999 | Singhvi |
| 5,989,027 A * | 11/1999 | Wagner et al. .............. 433/173 |
| 6,174,167 B1 * | 1/2001 | Wohrle ........................ 433/173 |

FOREIGN PATENT DOCUMENTS

WO    WO 95/12369    5/1995

OTHER PUBLICATIONS

Clark et al Development 108, 635–644 1990. Topographical Control of Cell Behavior: II multiple grooved substrate.
Chehroudi et al, *J. Biomedical Materials Research*, vol. 24, 1203–1219 (1990). Titanium–coated micromachined grooves of different dimensions affect epithelial cells differently in vivo.
Ricci et al, Mat. Res. Soc. Symp. Proc., vol. 252 (1992) The Influence of Surface Microgeometry on Fibroblast Colonization of Synthetic Surfaces.
Ricci et al, Meeting of Society of Biomaterials 1991, Tendon and Bone Cell Colony Formation on striated Surfaces.

* cited by examiner

*Primary Examiner*—Cary E. O'Connor
(74) *Attorney, Agent, or Firm*—M. K. Silverman

(57) ABSTRACT

A dental implant system includes an implant element for surgical insertion into a maxillofacial bone or tissue of a patient, the implant element having a collar section and a distal, anchor-like section, the collar section having an ordered microgeometric repetitive surface pattern in the form of alternating ridges and grooves, each having a fixed or established width in a range of about 2.0 to about 25 microns (micrometers) and a fixed or established depth in a range of about 2 to about 25 microns, in which the microgemoetric repetitive patterns define a guide for preferential promotion of the rate, orientation and direction of growth colonies of cells of the maxillofacial bone or tissue which are in contact with the surface pattern.

23 Claims, 10 Drawing Sheets

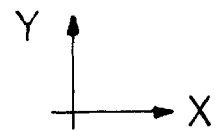
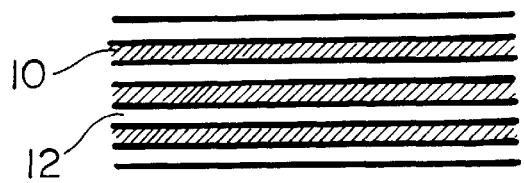
FIG. 1
FIG. 2
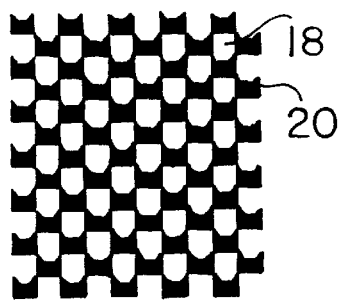
FIG. 3
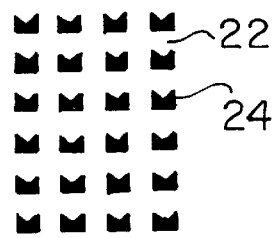
FIG. 4
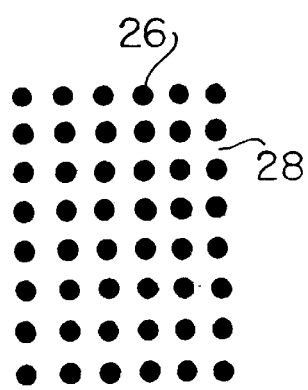
FIG. 5
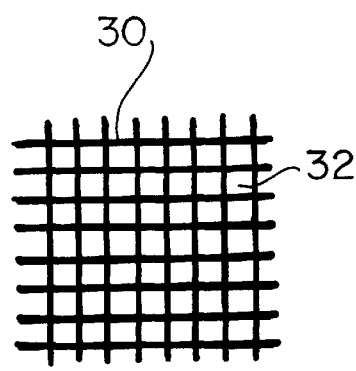
FIG. 6

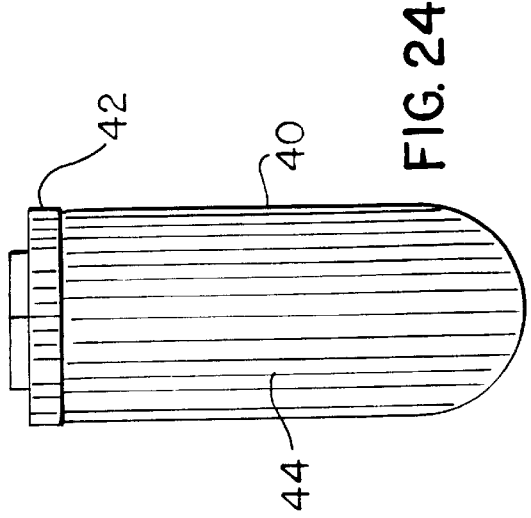
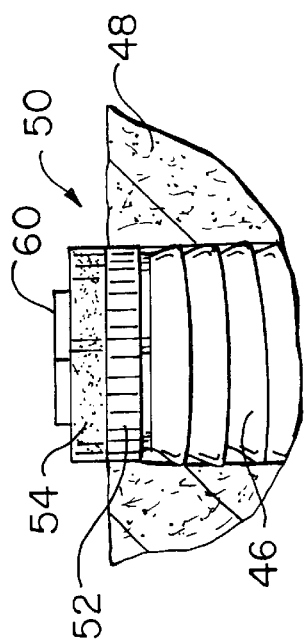
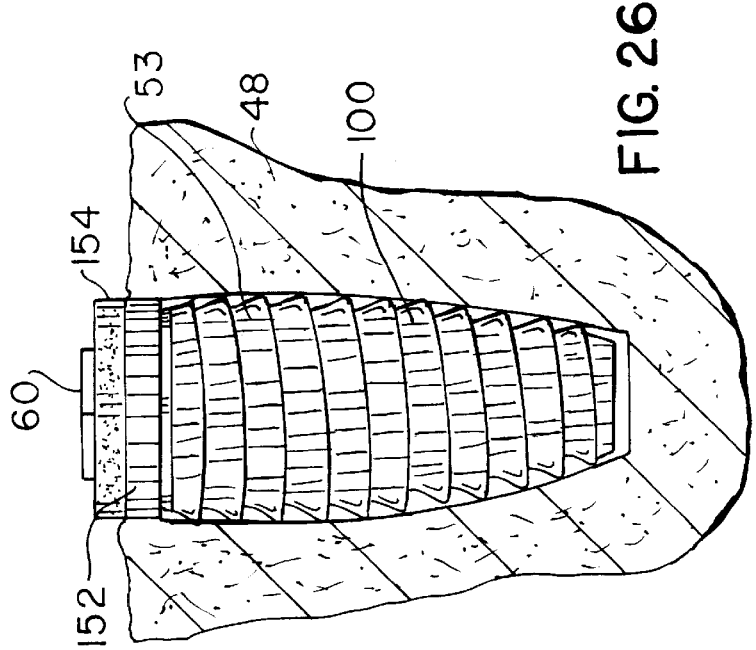

DENTAL IMPLANT SYSTEM WITH REPEATING MICROGEOMETRIC SURFACE PATTERNS

REFERENCE TO RELATED APPLICATION

This case is a continuation-in-part of application Ser. No. 08/996,244, filed Dec. 22, 1997 now abandoned, which is a continuation of application Ser. No. 08/639,712, filed Apr. 26, 1996, now abandoned which is a continuation of Ser. No. 08/390,805 filed Feb. 15, 1995, now abandoned which is a continuation of Ser. No. 08/146,790 filed Nov. 2, 1993, now abandoned.

BACKGROUND OF THE INVENTION

1. Field of Invention

The present invention relates to the provision of ordered repeating microgeometric patterns to bone and tissue interface zones of dental implants, to effect enhanced adhesion to soft tissue and osseointegration of an implant to bone.

2. Prior Art

Numerous publications establish that cell attachment growth, migration and orientation, as well as extracellular matrix synthesis and orientation thereof, are moderated by substrate surface shape (i.e., microgeometry) as well as by surface chemistry. However, the findings in such publications do not address what effect different substrate microgeometrics and dimension would have on various cell colonies' growth and migration parameters as opposed to the morphology of individual cells. Thus, while the prior art establishes that surface microgeometry of substrates influences cell orientation, it does not disclose or suggest what effect different surface microgeometry as implants would have on either the rate or direction of the cell colony growth of different cells of soft tissue or bone surrounding or abutting such a substrate.

Surface microgeometry interaction between soft tissue or bone and implant surfaces has been demonstrated on ceramic and metallic orthopedic implants. This interaction indicates that smooth implant surfaces promote the formation of thick fibrosis tissue encapsulation and that rough implant surfaces promote the formation of thinner, soft tissue encapsulation and more intimate bone integration. Smooth and porous titanium and titanium alloy implant surfaces have been shown to have different effects on the orientation of fibrous tissue or bone cells in vitro. In addition, surface roughness was demonstrated to be a factor in tissue or bone integration into implants having hydroxyapatite surfaces and to alter the dynamics of cell attachment and growth on polymer implants whose surfaces had been roughened by hydrolytic etching.

From the examination of in vitro growth characteristics of cells cultured on flat surfaces there have evolved the following cell "behavioral" characteristics:

1. attachment-dependent growth: the dependence of normal diploid cell or substrate attachment for normal growth;

2. density-dependent inhibition: the tendency of such cells to slow or stop growing once a confluent monolayer is formed;

3. substrate-exploring function: the ability of some types of cells to migrate on a surface in search of acceptable areas for attachment and growth; and 4. contact guidance: the ability of some types of cells to migrate and orient along physical structures. J. L. Ricci, et al Trans.Soc.Biomat. 17.253 (1991); J. L. Ricci, et al, *Tissue-Inducing Biomaterials*, Mat. Res. Soc. Symp. Proc. 252,221–229 (1992); J.Ricci, et al., *Bull.Hosp. Joint. Dis. Orthop. Inst. supra;* J. L. Ricci, et al, *J. Biomed Mater Res.* 25(5), supra.; D. M. Brunette, et al, J. Dent. Res., 11–26 (1986); P. Clark, et al. *Development,* 108, 635–644 (1990).

The behavioral characteristic of cellular contact guidance has been demonstrated in vitro on a variety of surfaces such as grooved titanium, grooved epoxy polymer, and collagen matrix materials of different textures and orientations. Grooved machined metal and polymer surfaces have also been shown to cause cellular and extracellular matrix orientation in vivo and to encourage or impede epithelial downgrowth in experimental dental implants. B. Cheroudi, et al. *J Biomat. Mater. Res.* 24. 1067–1085 (1990) and 22. 459–473 (1988); G. A. Dunn, et al supra; J. Overton, supra; S. L. Shor. supra; R. Sarber, et al, supra.

Substrates containing grooves of different configurations and sizes have been shown to have orientating effects on fibroblasts and substrates containing grooves of varying depth have been shown to have different degrees of effect on individual cell orientation establishing that grooved surfaces can modulate cell orientation in vitro and can cause oriented cell and tissue growth in vivo. For example, it has been shown that fibrous tissue forms strong interdigitations with relatively large grooves in the range of about 140 $\mu$m and can result in an effective barrier against soft tissue downgrowth perpendicular to the grooves. It has also been shown that smaller grooves on the order of about 3–22 $\mu$m were more effective in the contact guidance of individual cells. D. M. Brunette, et al. *Development,* supra; P. Clark et al, supra.

The findings in these publications do not address what effects different substrate microgeometries and sizes would have on various cell colonies growth and migration parameters as opposed to morphology of individual cells. That is, these publications do not disclose or suggest what effect different surface microgeometry of implants would have on either the rate or direction of the cell colony growth of different cells and different tissues surrounding an implant. In addition, these publications do not disclose or consider the most effective textured substrate or crude microgeometry for controlling cell colony growth.

The current methods used to texture the surfaces of dental implant elements typically employ sand, glass bead and alumina grit blasting techniques, and acid etching techniques, of the implant surface. In sand, glass bead or alumina grit blasting techniques, compressed air is generally used to drive a blasting medium onto the implant surface at a high velocity to deform and, in some instances, remove portions of the implant surface. The surface texture obtained depends upon the size, shape and hardness of the implant material and on the velocity at which the blasting medium is driven onto the implant surface. The most common surfaces produced by sand or glass bead blasting are matte or satin-finish, while alumina grit blasting produces a random roughened surface.

In acid etching techniques a pattern or mask is placed upon that surface of the implant desired not to be texturized. The exposed parts are then typically treated with an acid that corrodes the exposed surface of the implant whereupon the acid treated surface is washed or neutralized with an appropriate solvent and the pattern or mask is removed.

Illustrative of the sand or glass bead blasting technique is the method disclosed in U.S. Pat. No. 5,057,208 to H. R. Sherry, et al wherein the implant surface is shot blasted with metal shot followed by glass bead blasting and then electropolishing.

Illustrative of an acid etching technique is the method disclosed in U.S. Pat. No. 4,778,469 to R. Y. Lin, et al wherein an acid soluble (e.g., aluminum or zinc) space occupier is used. The space occupier contains the pattern to be transferred to the implant surface and is placed on the desired portion of the implant surface that is to be texturized. The space occupier is pressed into the implant surface and is then removed by treating it with acid.

It has been found that these typical blasting techniques leave debris from the processing materials embedded in the implant surface as contaminants. This debris has also been found in soft tissue isolated from the areas adjacent to failed press-fit total hip replacements indicating that the debris was released from the surface of the implants. These problems of residual contaminants debris have been overcome by using the use of laser systems which produces texturized microgeometric substrates without introducing embedded, particulate contaminants. See, for example, U.S. Pat. Nos. 5,645,740 and 5,607,607 to Naiman and Lamson. This instant invention refines and extends the teaching thereof with particular reference to dental implants. The prior art is also characterized by implants intended for use in soft tissue, such as U.S. Pat. No. 5,011,494 to Von Recum, et al and its related patent family. Therein, texturized surfaces of implants are provided with a variety of geometric configurations which comprise a plurality of projection and recesses formed in a three-dimensional body. It is therein specified that the mean bridging, breadth and diametric distances and dimension play a role in optimizing cell anchorage to implant surfaces. However, the teaching of Von Recum is not applicable to hard bone-like organic tissue, as exists in a dental implant environment.

Another reference which employs randomized roughing of an implant is U.S. Pat. No. 5,571,017 (1996) to Niznick which, although addressing the area of dental implants, does not employ an ordered or pre-established repetitive microgeometric surface pattern. Similarly, U.S. Pat. No. 4,320,891 (1982) to Branemark employs a randomly micro-pitted surface to create pores in a range of 10 to 1000 nanometers (one micrometer). See FIG. 36. Further, Branemark states that the optimal results in his system are obtained with pore diameters equal to or smaller than about 300 nanometers. Therein, although Branemark indicates that his implant surfaces may assume a pattern of grooves, corrugations or channels, such geometries are not ordered or repetitive, and it is apparent that the range of focus thereof is in the range of 0.3 to 1 micron in terms of diameters or width of such structures, whereas the lowest end of these invention relate to alternating ridges and grooves having a minimum width of six microns and extending in width to about 15 microns, the same based upon clinical studies as are more fully set forth below. Further, based upon the much smaller surface dimensions with which Brenemark is concerned, it is clear that the focus of Brenemark is that of individual cell growth, this as opposed to promotion of rate, orientation and direction of entire colonies of cells, i.e., the object of the present invention.

U.S. Pat. No. 4,752,294 (1988) to Lundgren refers to tissue ingrowth channels and openings having a dimension of about 30 microns. Accordingly, the dimension of interest to Lundgren is well in excess of the maximum dimension (25 microns) of concern in the present invention. Further, the teaching of Lundgrin is fundamentally that of a guide or element, of substantially three-dimensional character, for facilitating directed tissue regeneration. The present invention relates only to surface textures and does not address tissue regeneration.

U.S. Pat. No. 4,553,272 (1985) to Mears relates, as in Van Recum above, to the development of porous implants having pore sizes in a range of 25 to 400 microns, that is, a minimum range which is well in excess of the maximum range applicable to the ordered microgeometric repetitive surface patterns taught herein. Also, in view of the large dimension of the channels taught by Mears, no relationship exists or is suggested between cell size, structure size, and cellular control resultant thereof.

U.S. Pat. No. 5,004,475 (1991) to Vermeire relates to a hip prosthesis having channels or grooves which, similarly, to Mears, are intended to promote tissue ingrowth but which do not correlate between surface microgeometry, cell size, and cell growth. Further Vermeire does not teach any preferred structure or dimension for the channels or grooves thereof.

Patents such as U.S. Pat. No. 5,094,618 (1992) to Sullivan and 5,316,478 (1994) to Chalifoux teach the use of threaded dental post for endodontic use in association with dental restorations and improved securement between the restoration and a surviving tooth portion. Such references employ substantially random projections of a dimension much greater than that contemplated by the present invention, however, primarily differ from the in instant invention from the lack of teaching of ordered, repetitive, surface patterns within the applicable range in order to obtain advantageous characteristic of growth of colonies of cell at the interface between a maxillofacial bone and/or tissue and a dental implant and/or abutment element.

Thereby, all prior art of record addresses the issue of bone adhesion to an implant at either a level of tissue ingrowth entailing a dimension well above that set forth herein or relates to control of the growth or orientation of individual cells, as opposed to cell colonies, which resultingly require employment of surface characteristics of dimensions substantially smaller than that employed by the within inventors.

SUMMARY OF THE INVENTION

The invention relates to a dental implant system comprising implant element for surgical insertion into a maxillofacial bone or tissue of a patient, the implant element having a collar section and a distal, anchor-like section, said collar section having an ordered microgeometric repetitive surface pattern in the form or a multiplicity of alternating ridges and grooves, each having a fixed or established width in a range of about 2.0 to about 25 microns (micrometers) and a fixed or established depth in a range of about 2 to about 25 microns, in which said microgemoetric repetitive patterns define a guide for preferential promotion of the rate, orientation and direction of growth colonies of cells of said maxillofacial bone or tissue which are in contact with said surface pattern.

It is accordingly an object of the invention to provide microgeometic surfaces which alter the growth behavior of colonies of cells attached thereto.

It is another object to provide microgeometric surfaces of the above type having cross-sectional configurations, which are preferential to particular cell or tissue types.

It is a further object to provide microgeometric implant substrate for controlling in vivo cell attachment, orientation growth, migration and tissue function and therein having dimensions preferential for the prevention of cell growth in a first-axis and for the inducement of growth along a second axis.

It is a further object to provide repetitive microgeometric texturized configurations to implants applicable in a variety of medical applications.

The above and yet other objects and advantages will become apparent from the hereinafter-set forth Brief Description of the Drawings, Detailed Description of the Invention and Claims appended herewith.

BRIEF DESCRIPTION OF THE DRAWINGS

FIG. 1 is a plan diagrammatic view in an xy axis and at about 750 magnifications, showing ordered microgemetric surface patterns having parallel ridges and grooves, each of approximately equal width, in accordance with the present invention.

FIG. 2 is a view, similar to that of FIG. 1, however in which successive y-axis width of said ridges and grooves vary with y-axis direction of the surface pattern thereof.

FIG. 3 is a diagrammatic plan view of an ordered microgeometric surface pattern which defines a bi-axial x-y matrix formed of alternating recesses and projections along each axis.

FIG. 4 is a plan view, similar to that of FIG. 3, however showing a pattern in which all recesses and projections thereof are co-linear with each other.

FIG. 5 is a plan view, similar to that of FIG. 4, in which all ridges are circular in x-y cross-section.

FIG. 6 is a view, similar to that of FIGS. 3 thru 5, in which the grooves of the pattern define an xy grid as the surface pattern thereof.

FIG. 24 is an elevational view of a cylindrical dental implant in which all implantable surfaces thereof are provided with the same linear longitudinal microgeometric pattern.

FIG. 25 is an enlarged upper site view of a buttress thread implant in which the anchor portion thereof has not been provided with a surface pattern while the proximal or collar portion thereof has been provided with a first pattern for purpose of bone interface and a second pattern above the first pattern for purposes of soft tissue attachment.

FIG. 26 is a tissue breakaway view showing implantation of a buttress thread implant into bone in which the implant anchor and the lower portion of the collar thereof has been provided with a bone adhesion surface while an upper part of the proximal collar has been provided with a soft tissue adhesion surface.

DETAILED DESCRIPTION OF THE INVENTION

Bone Structure

Figure 7:
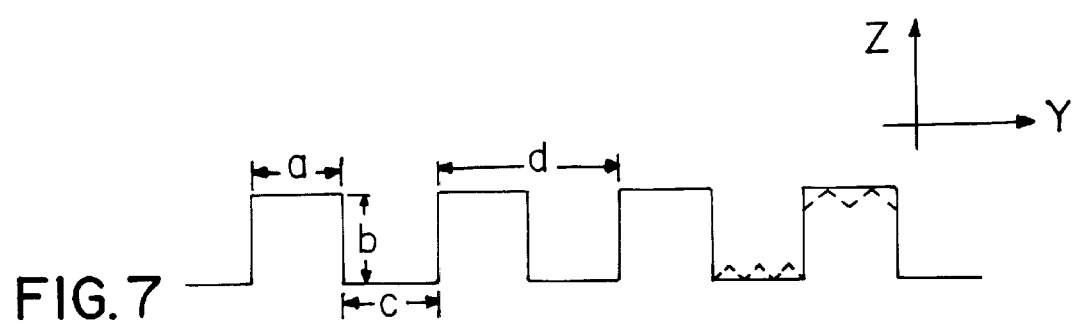
FIGS. 7 thru 14 are yz plane cross-sectional views of the patterns of FIGS. 1 thru 6 showing variations in yz plane geometry, that is, relationship of grooves to ridges that are applicable to one or more of the xy plane patterns shown in FIGS. 1 thru 6.

Bone tissue is the rigid supporting tissue constituting the principal component of almost all adult vertebrate skeletal structures. It exists in either dense or spongy form, known respectively as compact and cancellous bone. The typical bone cell size is of the order of about 10,000 nm, that is 10 microns.

Bone tissue consists of a chemical mixture of inorganic salts (65 to 70 percent) and various organic substances (30 to 35 percent) and is both hard and elastic. Its hardness is derived from inorganic constituents, principally calcium phosphate and calcium carbonate, with small amounts of fluorides, sulfates, and chlorides; its elasticity is derived from such organic substances as collagen, elastic cellular material, and fats. Internal tubular structures called Haversian canals contain nerve tissues and blood vessels that provide bones with organic nourishment. Surrounding these canals is a somewhat porous tissue composed of thin plates, known as lamellae, and usually containing cavities filled with a network of connective tissue called marrow or myeloid tissue. Bone marrow accounts for from 2 to 5 percent of the body weight of a person and consists of tissue of two types. Yellow bone marrow is made up principally of fat, and red bone marrow is tissue in which red and white blood cells and blood platelets originate. The external portions of bones, enclosing all the components mentioned above, include the compact and hardest of all bone tissue, which is in turn generally sheathed by a vascular, fibrous membrane known as the periosteum.

Micro-Texturing of Surface

With respect to bone and soft tissue adhering thereto, it has been found that the rate and direction of cell colony growth and the growth of different cell types surrounding surgical or dental implant can be controlled and effected by using the implants of this invention. In general, such implants comprise a plurality of separate zones of textured surface, each zone containing a different repetitive microgeometric design or pattern which is presented and exposed to the particular cell type for development of its unique colony growth. These different repetitive microgeometric textured design surfaces are intended to:

(a) promote the rate and orient the direction of bone growth, and discourage the growth of soft tissue to achieve secure fixation of the implant surface to bone tissue;

(b) promote the rate and orient the direction of the growth of soft tissue while discouraging the growth of bone tissue to achieve soft tissue integration with the implant surface; and/or (c) create a barrier that discourages the growth of soft tissue, particularly soft fibrous tissue, and thereby prevent the migration of soft tissue growth in bone tissue attachment surfaces of the implant.

The implants of the invention can be provided from suitable and acceptable materials that are commercially available such as cast or wrought cobalt and chrome alloys, various grades of commercial titanium, titanium alloys, stainless steel alloys, thermoplastic resins such as polyethyletherketone, polyphenylene sulfide, ceramics, alumina, as well as combinations thereof.

Example of Enhanced Bone Growth Surface to Direct Conduction of Bone Tissue

A surface consisting of 12-μm groove and ridges has been shown to increase the RBM (rat bone marrow) to RTF (rat tendon fibroblast) cell colony growth ratio to encourage bone cell growth over fibrous tissue growth. In addition, this surface caused specific directional migration of bone cells at approximately twice the rate of cells on a flat surface. This surface can be used to enhance bone versus soft tissue growth as well as to direct bone growth into regions of an implant surface where bone fixation is needed.

Example Surfaces for Stimulation of Fibrous Tissue Growth

Since fibrous tissue and bone cells generally "compete" for surface areas, the ratio of bone to soft tissue colony area increase, on a given surface, is an important parameter in surface selection. The ratio indicates the relative stimulation or inhibition of cell growth on these surfaces (see FIG. 20). Theoretically, this ratio would be significant to provide advantage for growth of one or another cell type on a surface, with high ratios favoring bone cell growth and low ratios favoring fibrous tissue growth. Based on these ratios, a 2-micron indentation or groove provided a 32.8% decrease in bone/soft tissue growth, providing a significant advantage in soft cell tissue growth. The surface could be used to increase fibrous tissue cell growth; it can also be used to significantly orient growth of these cells. A 4-micron indentation or groove surface provided a similar ratio, but it is based on lower overall growth rates. Therefore, if non-oriented fibrous cell growth is required, a flat control surface provides an inherent advantage to RTF tissue cells at a ratio of bone to soft tissue cell growth of approximately 0.6. This effect has been observed in vivo where smooth surfaces have been shown to favor formation of thick fibrous tissue capsule formation as compared to textured surfaces of the same composition, which show less fibrous capsule formation and more extensive osteointegration.

Example of Surfaces for Stimulation of Bone Tissue Growth

Figure 21:
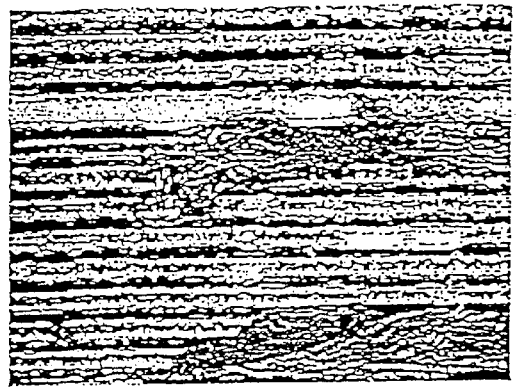
Figure 22:
FIGS. 22 and 23 are higher magnification micrographs of deproteinated bone/implant specimen showing bone growth into the grooves of the inventive microgeometric surface patterns.
Figure 23:

The surface having the highest ratio of bone to soft tissue cell growth is the 12-μm/micron indentation or groove substrate. The basis of the ratio is the fact that this surface inhibits soft tissue colony growth by 53.1% relative to controls (FIG. 21). This is close to the maximal suppression of soft tissue cell growth seen on such microgeometries. The same surface, however, does not maximally suppress bone cell growth (46.3% suppression relative to controls). See FIGS. 22 and 23. The differential suppression results in a 14.4% increase in bone/soft tissue growth relative to the control ratio. Where both cell types are present and compete for growth, this provides a significant advantage to bone colony growth. Bone cells grown on this surface also exhibits greatly enhanced directional growth in the x-axis. Such an in vivo surface favors bone over soft tissue growth and can be used to conduct directional bone growth.

The textured substrates were further studied to determine the preferable substrates and their structure for control of cell growth. The study was conducted to determine the effect of a range of grooves on the control of cell growth.

Cell Orientation and Migration

Figure 20:
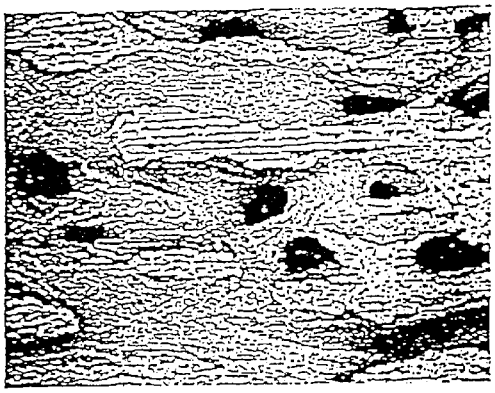
FIGS. 20 and 21 are scanning electron micrographs at about 750 magnifications of a deproteinated bone specimens from a bone to metal implant showing the surface of the implant after bone removal (FIG. 20) and the surface of the bone after implant removal (FIG. 21) both show bone ingrowth into microgrooves within the bone implant surface, the width of such grooves being about 12 microns.

The experimental surfaces were observed to cause oriented cell attachment and migration, resulting in elongated colony growth, which was accelerated in the x-direction (parallel to the axis of surface microgeometry) and inhibited in the y-direction (perpendicular to the axis of surface microgeometry) as shown in FIGS. 20–21. On an individual cell level, the cells appeared to be "channelled" in the x-direction, as compared with control culture where outgrowing cells move randomly on flat surfaces. The most efficient "channelling" was observed on the 6-μm and 8 μm surfaces. On these surfaces, both hard and soft cell types were observed to attach and orient within the grooves. This resulted in enhanced x-axis growth and almost no y-axis growth by both cell types on these surfaces.

On smaller microgeometries, a different effect was observed. Both the RBM and RTF cells bridged the surfaces on the 2 μm grooves resulting in cells with different morphologies than those on the 6-, 8-, and 12-μm surfaces. These cells were wide and flattened and were not well oriented. On the 4-μm grooves, the rat bone marrow and RTF cells showed mixed morphologies, with most cells aligned and elongated but not fully attached within the grooves. This resulted in appreciable y-axis growth of the bone marrow cells on the 2-μm surfaces and by the RTF cells on the 2- and 4-μm surfaces. At the other end of the size range, limited y-axis growth was also observed when these cell types were grown on the 12-μm surfaces. This may be a result of the cell orientation and cell "wraparound" resulting in limited y-axis growth.

The results of the observed effects of these surfaces on overall bone marrow and RTF cell colony growth were pronounced. All the experimental substrates caused varying but significant increases in x-axis growth compared to the diameter increase of the controls and varying but pronounced inhibition of y-axis growth. (FIGS. 21).

Importantly, suppression of cell growth differed between cell types. This offers the opportunity to differentially provide a growth advantage to one cell type over the other.

With reference to the means by which the above set forth principles and experimental data may be reduced to practice, it has been found that a dental implant system which includes at least an implant element and, in a given application, an abutment element, may be selectably surfaced in the fashion illustrated in FIGS. 1 thru 6 which show a variety of patterns which may comprise ordered microgeometric, repetitive surface patterns, and which may be applied to materials inclusive of titanium, stainless steel, plastics, ceramics, biocompatible glass and combinations thereof which materials may be coated with coatings inclusive hydroxyapatite, RBM roughening, titanium, plama sprayed, calcium sulfate, biocompatible glass, collagen, growth factor compounds, and combination thereof. More particularly, with reference to FIG. 1, the subject ordered microgeometric repetitive patterns may take the form of a multiplicity of alternating grooves 10 and ridges 12 in which each respective ridge and groove displays a width between about 6.0 to about 25 microns and a depth in a range between about 2 to about 25 microns. In the embodiment of FIG. 1, an infinite repeating pattern of co-parallel linear ridges and grooves having substantially equal width defines a micro textured surface of an implant or substrate as contemplated by the instant invention.

In the embodiment of FIG. 2 is shown a surface in which alternating ridges 14 and grooves 16 increase y-axis in width with reference to a transverse axis relative to the axis of said ridges and grooves. Accordingly, with reference to types of tissues with which a transition of tissue type or gradient of tissue density exists, a textured surface of the type of FIG. 2 may be employed.

In FIG. 3, is shown a surface pattern in which ridges 18 take the form of projections while grooves 20 take the form of recesses to thereby define a checkerboard configuration. Therein such ridges and grooves alternate with reference to both a x and y axes of a given surface.

The embodiment of FIG. 4 differs from that of FIG. 3 in that ridges 22 thereof form a bi-axial linear pattern. Similarly, grooves 24 of the embodiment of FIG. 4 define a x-y matrix formed of recesses that may assume a number of geometries.

In FIG. 5 is shown embodiment of the invention in which circular depressions 26 define grooves or depressions while the areas therebetween, namely, spaces 28 define ridges or projections. It may, therefrom be appreciated that the terminology "alternating ridges and grooves," as used herein, encompasses a variety of microtexturized geometric patterns in which the ridges and grooves thereof while alternating relative to each other may themselves comprise any one of a variety of geometries inclusive of channels, rectangles, parallelograms, squares, circles and ovals.

With reference to FIG. 6, there is shown a grid like arrangement in which grooves 30 define an xy matrix which is etched into a surface 32 such that surface 32, when viewed relative to etched grooves 30, comprises ridges.

From the embodiment of FIGS. 1 thru 6 it may be appreciated that the width (or diameter) of a given groove need not correspond to that of its respective ridge, providing such widths fall within the above-referenced range of about 2 to 25 microns with a depth in a range of about 2 to about 25 microns. It has, thereby, through extensive experimentation as set forth above, been determined that a microgeometric repetitive pattern within the scope of the present invention may define a guide for preferential promotion of the rate, orientation and directionality of growth of colonies of cells of maxillofacial bone or tissue without requirement that the width of a ridge be equal to that of a groove in that it is, essentially, the groove of the microtexturized surface that defines the guide for preferential promotion of growth of colonies of cells. In most applications, it is desirable to maximize the density of grooves upon a given surface to thereby attain the desired cell growth effect; however, differing clinical environments will dictate use of different surface patterns and density if distribution of grooves.

Figure 8:
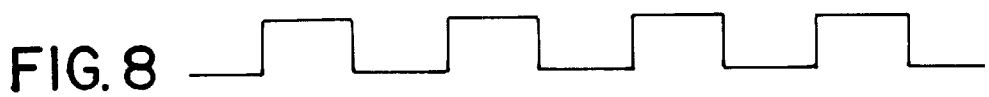
Figure 9:
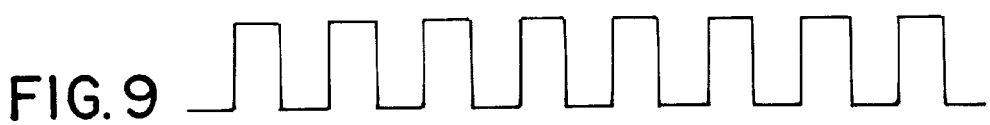

With reference to the views of FIGS. 7 thru 14, there is shown diagrammatic cross-sections which may be employed in association with the microgeometric textured configurations above described with reference to FIGS. 1 thru 6. In other words, the views of FIGS. 7 thru 14 illustrate the range of geometries which may be defined within the yz plane of the surface patterns. Resultingly, FIGS. 7 thru 9 show variations in ridge width a, ridge and groove height b, and groove width c. Typically, ridge height will equal groove depth. Parameter d is the sum of ridge and groove width.

The right side of FIG. 7 indicates that y-axis surfaces need not be linear.

Figure 10:
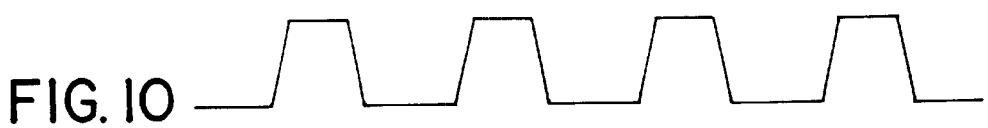
Figure 11:
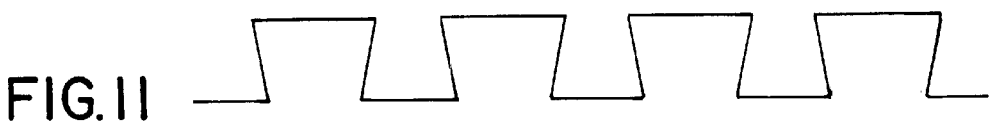
Figure 12:
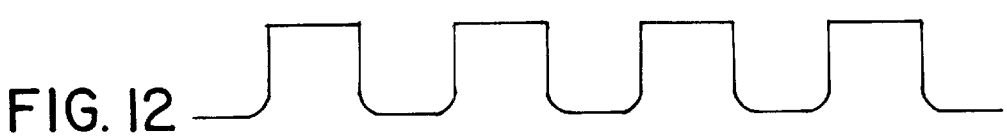
Figure 13:
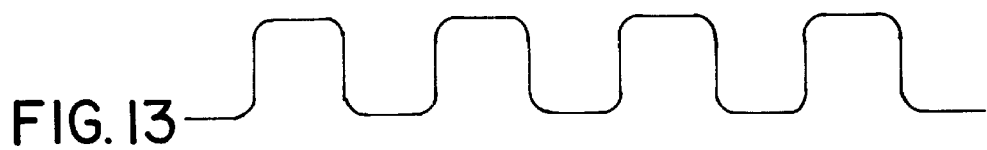
Figure 14:
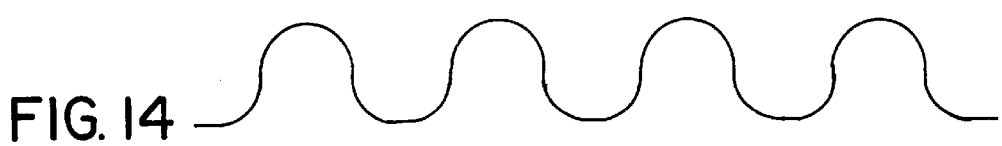
Figure 15:
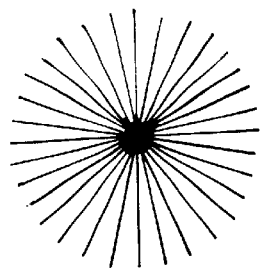
FIGS. 15 thru 19 show further xy plane surface patterns which, respectively, comprise radiating, concentric, circular, radiating fan, radiating with concentric, and radiating with intersecting polar, patterns.

FIGS. 10 and 11 show that the walls of the ridges and/or grooves may be yz sloped either inwardly or outwardly relative to the z-axis. FIGS. 12 and 13 show that the transition from a y-axis ridge surface to a groove surface need not be a sharp one but, rather, may be curved. In FIG. 14 is shown a cross-sectional view of a pattern in which all yz surfaces are sinusoidal. In such embodiment, the potential for "bridging" between lines of cell colony growth is maximized since an abrupt delineation between ridges and grooves is not present.

Figure 16:
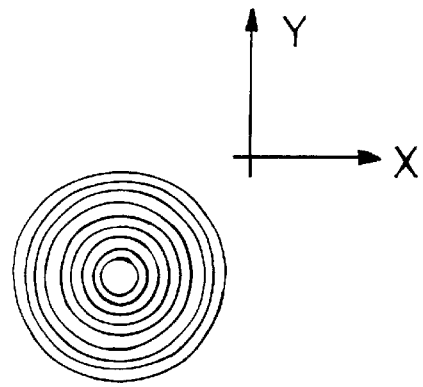
Figure 17:
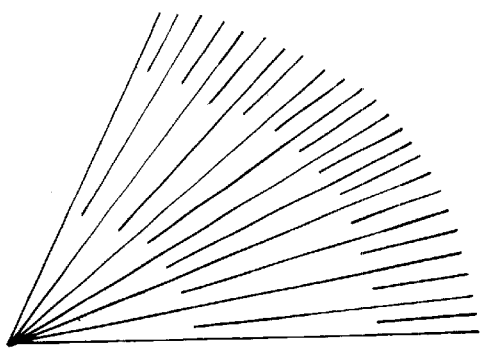
Figure 18:
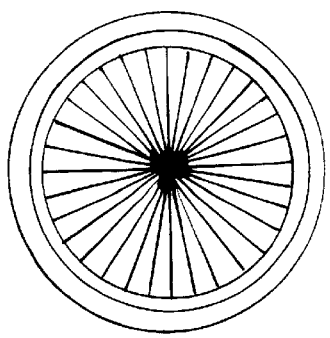
Figure 19:
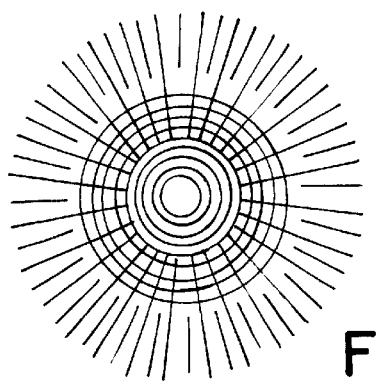

Shown in FIGS. 15 thru 19 are further xy surface patterns which are programmable through the use of processes selected from the process group consisting of laser etching, acid etching, mechanical etching and photolithography. More particularly, FIG. 15 comprises a radiating pattern. FIG. 16 a concentric circular pattern, FIG. 17 a radiating fan pattern, FIG. 18 a radiating/concentric pattern, and FIG. 19 a radiating pattern with an intersecting polar pattern. It is, therefrom, to be appreciated that an ordered microgeometric repetitive surface pattern may, within the scope of the invention, assume a wide variety of unidirectional linear, bi-axial linear, radial, radial and polar, non-linear, and differential linear or polar patterns.

With reference to FIG. 24, there is shown a simple cylindrical implant element 40 of the present dental implant system in which both a platform section 42 and an anchor section 44 thereof are provided with a unidirectional linear repetitive surface pattern of the type of FIG. 1 above taken in combination with any of the cross sectional geometries of FIGS. 7 thru 14 above. Therein, a multiplicity of alternating ridges and grooves is applied to the entire lateral surface of implant 40 along an axis which is co-axial with the axis of surgical insertion of the implant into a maxo-facial bone or tissue.

In FIG. 25 is shown an upper portion of a buttress thread implant 46 which has been surgically inserted into bone 48. However, in the embodiment of FIG. 25, the anchor section has not been microtexturized while platform section 50 thereof has been provided with a first ordered microgeometric repetitive surface pattern as to a distal section 52 thereof while a proximal portion 54 has been provided with a second ordered geometric pattern more suitable for purpose of tissue (as opposed to bone) adhesion or interface. Such a second ordered pattern exhibits a width of about 2 to about 25 microns and a depth in a range of about 2 to about 25 microns in that it has been determined that tissue, such as gum tissue, is more amenable to preferential promotion of rate, orientation and directionality of growth of colonies of cells if the width of grooves is somewhat smaller than that above discussed with reference to bone adhesion and interface.

With reference to FIG. 26, there is shown a further buttress thread implant 100 which has been surgically inserted within bone 48. However, in the embodiment of FIG. 26, the entire lateral surface of the anchor of the buttress thread implant has been furnished with the same first ordered repetitive surface 52 above described with reference to FIG. 25. Further, proximal region 154 has been provided with a surface more suitable to tissue adhesion interface, namely, said second ordered pattern, while lower region 152 has been provided with the same pattern as anchor surface 53. At the top of each of the implants of FIGS. 24 to 26 is shown a gripping surface 60 used for purposes of surgical insertion and for complemental receipt of an abutment element of a dental implant system.

Figure 27:
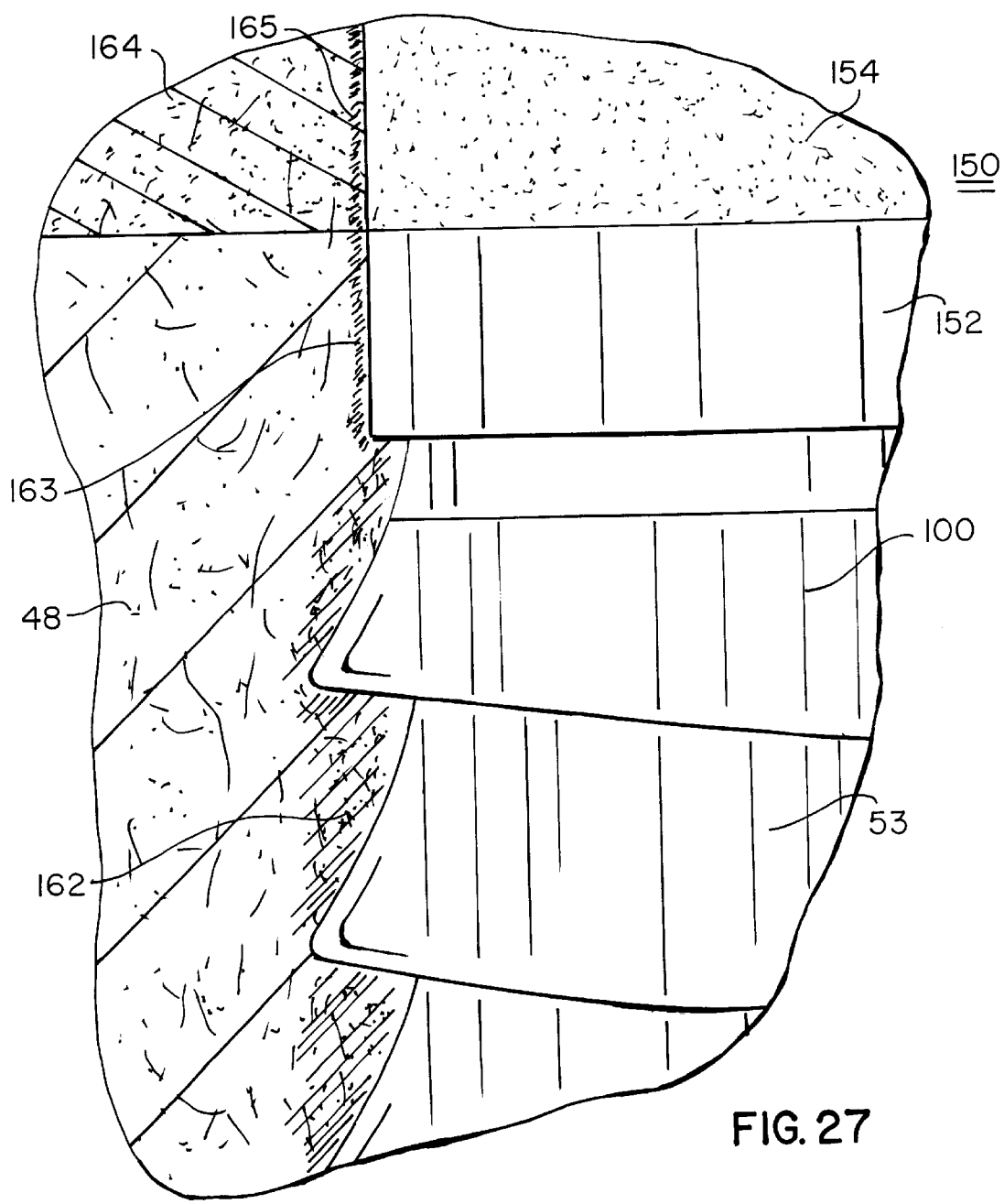
FIG. 27 is an enlarged view showing bone and tissue adhesion interfaces using the structure of FIG. 16.

FIG. 27 comprises an enlarged view of a bone adhesion interface 162 which exists between bone 48 and the first ordered microgeometric repetitive of the anchor 53 of the implant of 100. Also shown therein are lower and upper regions 152 and 154 of platform section 150 of the implant as well as an interface 165 of said upper region 154 with gum tissue 164. Further shown is adhesion interfaces 163 between bone 48 and lower region 152 of platform 150. Therefrom may be appreciated the effect of the inventive microgeometric repetitive surface patterns in the formation of bone and tissue adhesion interfaces, that is, the effect of which is to strengthen bone and tissue in the regions immediately surrounding a dental implant element.

Micro-geometric patterns of this type may be formed by various methods, including, without limitation, laser etching, acid etching, mechanical etching, and photo-lithography.

Figure 28:
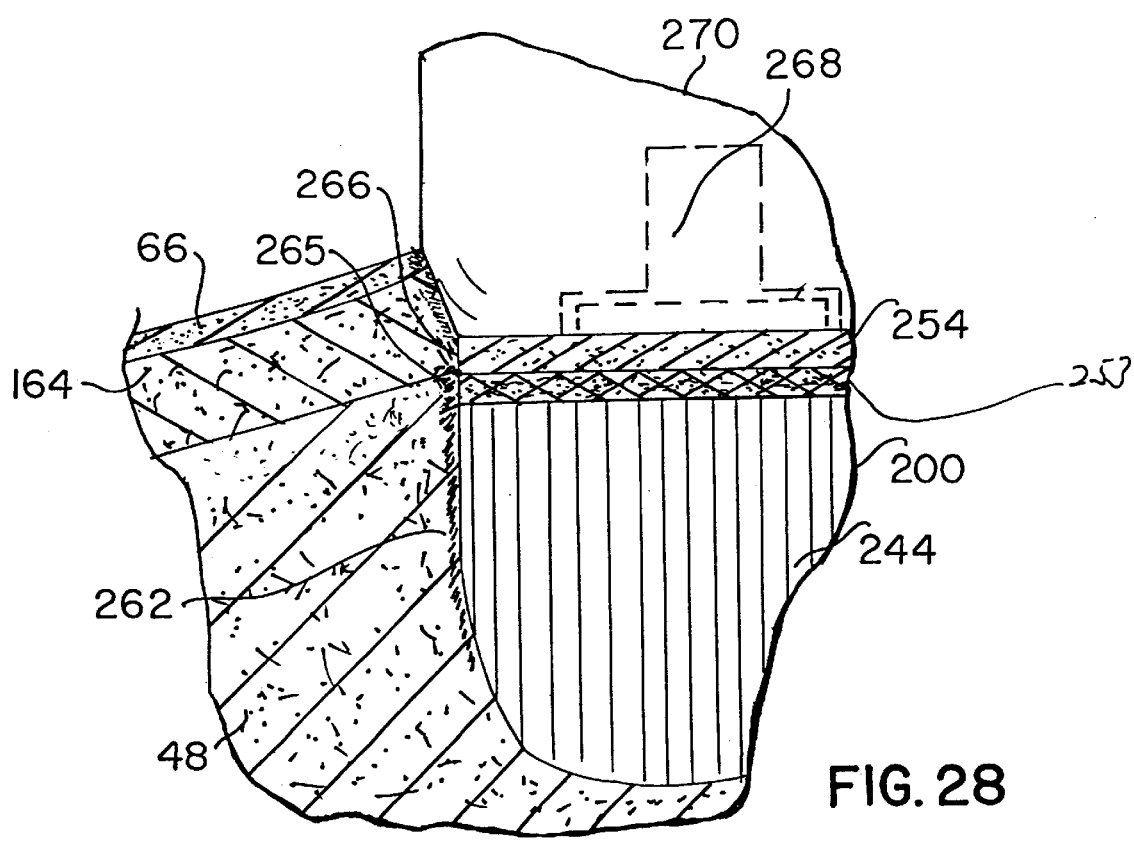
FIG. 28 is a tissue breakaway view showing implantation of an implant into bone including an abutment, in which all implant and abutment surface have been provided with bone or tissue adhesion interfaces respectively.

The above may be more fully appreciated with reference to the view of FIG. 28, which is similar to the views of FIGS. 26 and 27, but for the use of a textured cylindrical anchor 244, as opposed to a buttress thread anchor section, of a dental implant 200. However, additionally shown in the embodiment of FIG. 28 is gingival epithelium 66 above gum tissue 164 also referred to as the connective tissue, between the epithelium and the cortical bone 48. Further shown in FIG. 28 is an abutment 270 (secured upon implant projection 268) of a dental implant system, that has been provided with collars 254 having a microtexturized regions 266 to effect gum and epithelium tissue adhesion interfaces thereto. Also, a collar 253 of implant 200 has been provided with a microtexturized surface particularly adapted for bone adhesion interface 265. It may, accordingly, from the view of FIG. 28, be appreciated that in a given application as many as five different microtexturized surfaces may be employed to maximize bone and tissue adhesion to one or another portion of an implant element and/or of an abutment element of a dental implant system. As such, different patterns of tissue or bone interface and adhesion, that is, differing forms of promotion of rate, orientation and directionality of growth of contacting colonies of cells will be achieved with reference to differing micro-textured surfaces of the implant material. Such interfaces are indicated by numerals 262 (implant anchor to bone interface), 265 (implant collar to bone interface), 266 (collar to gum) 272.

Figure 29:
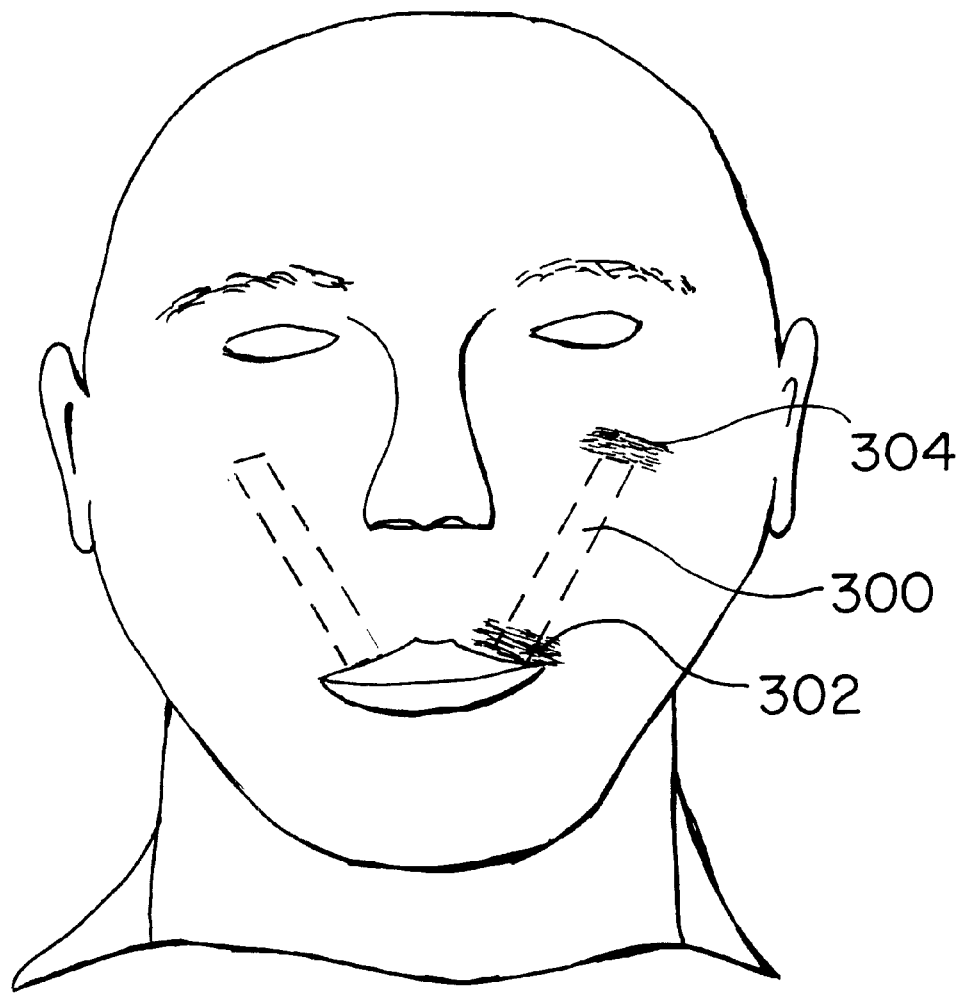
FIG. 29 is a schematic view showing the use of an elongated maxillofacial implant to support the maxilla bone relative to the sinus complex.
Figure 30:
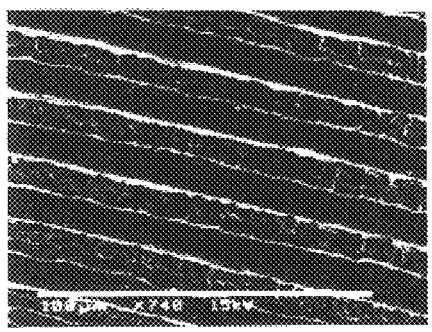
FIG. 30 is an enlarged view of a buttress thread dental implant, of the type of FIG. 26, which has been provided with the inventive ordered microgeometric surface on the collar.

With reference to FIG. 29 there is shown the manner in which an implant 300 may be used as a means of surgical support of a maxillofacial bone 302 by securement thereof to a bone 304 of the sinus complex. Such implant is of value in the area of reconstructive surgery and in dental procedures in which the cortical bone lacks sufficient strength or stability to otherwise receive and hold an implant element. In the application of FIG. 29, the upper and lower ends of the implant 300 will be provided with microtexturized surfaces as above described.

In FIGS. 30 thru 36 are shown micrographs of the inventive microgeometric surfaces at magnifications ranging from 600 to 1700.

Figure 31:
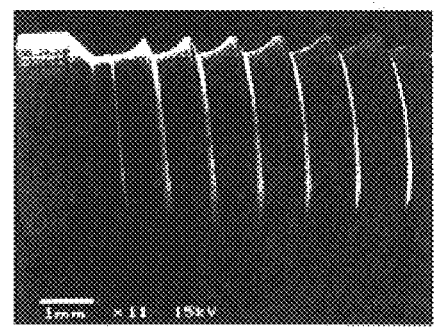
FIG. 31 is an enlargement (at 170 magnifications) of the collar portion of FIG. 30, showing a pattern of continuous grooves and ridges, as depicted in FIG. 1 above.
Figure 32:
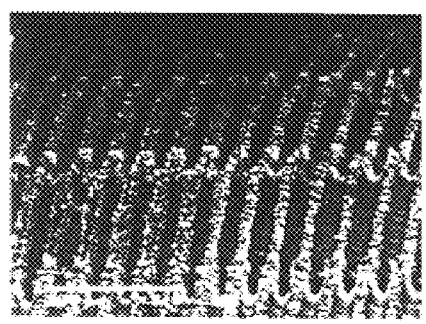
FIG. 32 is an electron micrograph showing use of ax-axis discontinuous ridges and grooves, in both x and y axes, therein corresponding to the pattern of FIG. 3 above.
Figure 33:
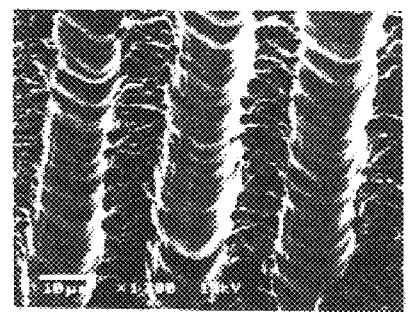
FIG. 33 is an electron micrograph, however, at 1,700 magnifications, of the views of FIGS. 32 or 34 below.
Figure 34:
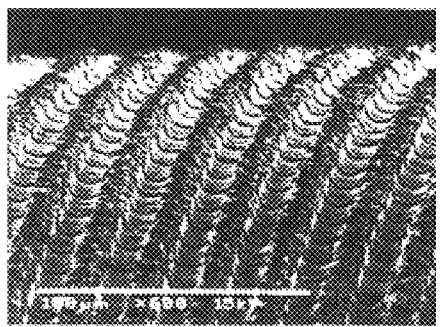
FIG. 34 is an electron micrograph of the surface pattern upon the collar of an implant similar to that shown in FIG. 30 in which the grooves thereof are continuous, as opposed to the x-axis discontinuous ridge and groove segments of FIG. 32, employed upon the collar of the implant of FIG. 35 below.
Figure 35:
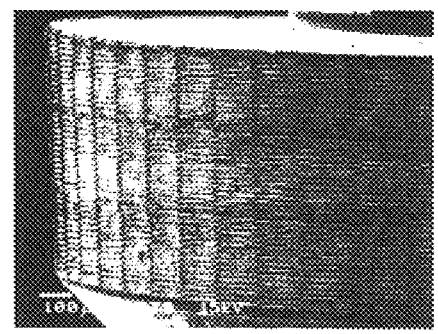
FIG. 35 is a 600-power electron micrograph enlargement of the collar of the implant shown in FIG. 32. This was photographed on an angle to show ridge height and groove depth.
Figure 36:
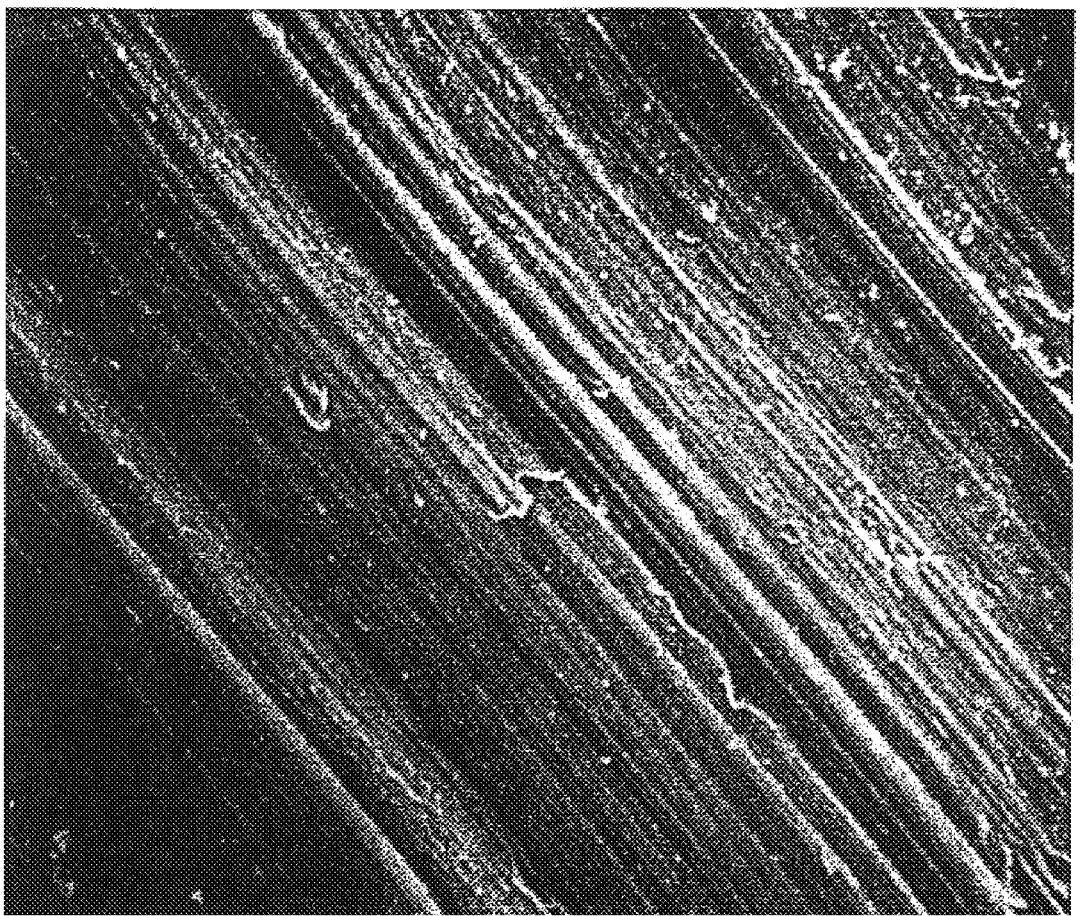
FIG. 36 is a micrograph of a prior art microgeometric surface pattern showing the randomness of such pattern.

FIG. 31 is an enlarged view of a buttress thread dental implant, of the type of FIG. 26, which has been provided with the inventive ordered microgeometric surface. FIG. 35 is an enlargement at 170 magnifications of the collar portion of FIG. 31, showing a pattern of discontinuous grooves and ridges, as depicted in FIG. 1 above FIG. 32 is an electron micrograph comprising a further enlargement of the collar of FIG. 31, showing use of alternating ridges and grooves in both x and y axes, therein corresponding to the pattern of FIG. 3 above. FIG. 32 is an electron micrograph, however, at 1,700 magnifications, of the view of FIG. 31. FIG. 34 is an electron micrograph of the surface pattern upon the thread structure of the implant of FIG. 30 in which the grooves thereof are continuous, as opposed to the discontinuous ridge and groove segments of FIG. 32, employed upon the collar of the implant of FIG. 30. FIG. 35 is a 600-power electron micrograph enlargement of the collar of the implant shown in FIG. 34. In all figures, the small longitudinal grooves therein reflect laser-related melting, rather than a part of the microgeometric surface of the implant.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the claims appended herewith.

We claim:

1. A dental implant system comprising an implant element for surgical insertion into a maxillofacial bone and tissue of a patient, said implant element having a collar section and a distal, anchor-like section, said collar section having a first ordered microgeometric, repetitive surface pattern in a form of a multiplicity of alternating ridges and grooves, each having an established width in a range of about 2 to about 25 microns, and an established depth in a range of about 2 to about 25 microns, each groove having a base and a wall, each groove defining, in radial cross-section, a relationship of groove base to grove wall that is equal to, or less than, about ninety degrees;

whereby said micro-geometric repetitive pattern defines a guide for a preferential promotion of the rate, orientation and direction of growth of colonies of cells of said maxillofacial bone or tissue, which are in contact with said surface pattern.

2. The dental implant system as recited in claim 1, in which said distal anchor-like section of said implant element also comprises said first repetitive micro-geometric pattern thereupon.

3. The dental implant system as recited in claim 1, in which an uppermost region of said proximal section comprises a second ordered micro-geometric pattern of ridges and grooves in a range of width of between about 2 and about 25 microns, and a depth in a range of about 2 to 25 microns, said upper region of said proximal section defining a soft tissue adhesion interface, and in which a lower region of said proximal section comprises said first pattern of alternating ridges and grooves, lower region constituting a bone adhesion interface.

4. The dental implant system as recited in claim 1, further comprising an abutment element proportioned for complemental engagement with said implant element, or as an extension of the implant platform, said abutment including a tissue adhesion zone defined by an ordered microgeometric repetitive pattern in the form of a multiplicity of alternating ridges and grooves having established widths in a range between about 2 and about 25 microns, and an established depth in a range of about 2 to 25 microns.

5. The system as recited in claim 4 in which base materials of said abutment elements are selected from the group consisting of the materials of commercially pure titanium, titanium alloys, stainless steel, plastics, ceramics, biocompatible glass and combinations thereof.

6. The system as recited in claim 4 in which base materials of said implant elements are selected from the group consisting of the materials of titanium and alloys thereof, stainless steel, ceramics biocompatible glass and combinations thereof.

7. The dental implant system as recited in claim 6 in which said repetitive micro-geometric pattern comprises a product of the process selected from the process group consisting of laser etching, acid etching, mechanical etching, and photolithography.

8. The system as recited in claim 1 in which said repetitive micro-geometric pattern of ridges and grooves comprises application to surfaces of said implant element in orientations which, relative to a longitudinal axis of said implant system, are selected from the group consisting of vertical, horizontal, diagonal, radial, circumferential, and concentric orientations.

9. The dental implant system as recited in claim 8 in which a surface of said implant element comprises a coating selected from the group of surfaces consisting of hydroxyapatite, RBM roughening, titanium, plama sprayed, calcium sulfate, biocompatible glass, collagen, growth factor compounds, and combination thereof.

10. The dental implant system as recited in claim 1 in which said pattern of ridges and grooves define substantially parallel geometries thereof.

11. The dental implant system as recited in claim 10 in which said pattern is grid-like.

12. The dental implant system as recited in claim 1, in which said pattern of ridges and grooves define a radial geometry.

13. The system as recited in claim 12 in which said pattern further includes polar geometries.

14. The dental implant system as recited in claim 1, in which said pattern of ridges and grooves defines polar geometries.

15. The system as recited in claim 1 in which said maxillofacial bone includes mandible cortical or maxillofacial bone.

16. The system as recited in claim 15 in which said implant element exhibits a radial longitudinal cross-section selected from the group of geometries consisting of screw-like, tapered screw, cylindrical, tapered cylindrical, buttress thread, and reverse buttress thread.

17. The dental implant system as recited in claim 1, in which a radial cross-section of said ridges and grooves comprises a sinusoidal cross-section.

18. A dental implant system comprising an implant element for surgical insertion into a maxillofacial bone and tissue of a patient, said implant element having a collar section and a distal, anchor-like section, said anchor section having a first ordered microgeometric, repetitive surface pattern in a form of a multiplicity of alternating ridges and grooves, each having an established width in a range of about 2 to about 25 microns, and an established depth in a range of about 2 to about 25 microns, each groove having a base and a wall, each groove defining, in radial cross-section, a relationship of groove base to groove wall that is equal to, or less than, about ninety degrees, whereby said micro-geometric repetitive pattern defines a guide for a preferential promotion of the rate, orientation and direction of growth of colonies of cells of said maxillofacial bone or tissue, which are in contact with said surface pattern.

19. The dental implant system as recited in claim 18, in which said collar section of said implant element also comprises said first repetitive micro-geometric pattern thereupon.

20. The dental implant system as recited in claim 17, in which an uppermost region of said proximal section comprises a second ordered micro-geometric pattern of ridges and grooves in a range of width of between about 2 and about 25 microns, and a depth in a range of about 2 to 25 microns, said upper region of said proximal section defining a soft tissue adhesion interface, and in which a lower region of said proximal section comprises said first pattern of alternating ridges and grooves, lower region constituting a bone adhesion interface.

21. The dental implant system as recited in claim 18, in which a radial cross-section of said ridges and grooves comprises a sinusoidal cross-section.

22. A dental implant system comprising an implant abutment comprising a body for surgical insertion into a maxillofacial bone having a collar section having an ordered microgeometric, repetitive surface pattern in a form of a multiplicity of alternating ridges and grooves, each having an established width in a range of about 2 to about 25 microns, and an established depth in a range of about 2 to about 25 microns, each groove having a base and a wall, each groove defining, in radial cross-section, a relationship of groove base to grove wall that is equal to, or less than, about ninety degrees, whereby said micro-geometric repetitive pattern defines a guide for a preferential promotion of the rate, orientation and direction of growth of colonies of cells of said maxillofacial tissue, which are in contact with said surface pattern.

23. The dental implant system as recited in claim 22 in which a radial cross-section of said ridges and grooves comprises a sinusoidal cross-section.

\* \* \* \* \*

UNITED STATES PATENT AND TRADEMARK OFFICE
CERTIFICATE OF CORRECTION

| | | |
|---|---|---|
| PATENT NO. | : 6,419,491 B1 | Page 1 of 1 |
| APPLICATION NO. | : 09/500038 | |
| DATED | : July 16, 2002 | |
| INVENTOR(S) | : John Ricci et al. | |

It is certified that error appears in the above-identified patent and that said Letters Patent is hereby corrected as shown below:

On the Title page, Item [63], delete

"Related U.S. Application Data

Continuation-in-part of application No. 08/996,244, filed on Dec. 22, 1997, now abandoned, which is a continuation-in-part of application No. 08/639,712, filed on Apr. 26, 1996, now abandoned, which is a continuation of application No. 08/390,805, filed on Feb. 15, 1995, now abandoned which is a continuation of application No. 08/146,790, filed on Nov. 2, 1993, now abandoned."

Signed and Sealed this
Fifteenth Day of March, 2011

David J. Kappos
*Director of the United States Patent and Trademark Office*